United States Patent [19]

Trone et al.

[11] 3,985,509

[45] Oct. 12, 1976

[54] FLAME IONIZATION DETECTOR WITH FLAME MONITOR

[75] Inventors: Elmer Trone, Benecia; Robert Leslie Howe, Livermore, both of Calif.

[73] Assignee: Varian Associates, Palo Alto, Calif.

[22] Filed: Feb. 13, 1976

[21] Appl. No.: 657,789

[52] U.S. Cl. .......................................... 23/254 EF
[51] Int. Cl.² ........................................ G01N 31/12
[58] Field of Search ........ 23/254 EF, 232 C, 232 E, 23/254 E

[56] References Cited
UNITED STATES PATENTS

| | | | |
|---|---|---|---|
| 3,086,848 | 4/1963 | Reinecke | 23/254 EF |
| 3,340,013 | 9/1967 | Rooney et al. | 23/254 EF |
| 3,597,162 | 8/1971 | Reinecke | 23/254 EF |

Primary Examiner—Robert M. Reese
Attorney, Agent, or Firm—Stanley Z. Cole; Gerald M. Fisher; John J. Morrissey

[57] ABSTRACT

A flame ionization detector including means for monitoring the flame condition, so as to enable ignition of an extinguished flame. An igniter coil is mounted proximate the burner nozzle of the FID, and thermocouple means are provided including a hot junction in thermal contact with the nozzle, and a spaced cold junction. Means are provided for applying an electrical potential to the igniter coil to enable ignition of the flame upon a flame-out condition being detected as measured by the thermocouple output. In a preferable embodiment, the ends of the igniter coil are connected to a pair of electrical leads, with the connection zones defining the hot and cold junctions of the thermocouple. This permits the same lead pair to provide both the potential enabling the igniter function of the coil, and the interconnection for the thermocouple output signal. The same lead pair may also be utilized to provide the biasing potential to the burner nozzle.

14 Claims, 3 Drawing Figures

FLAME IONIZATION DETECTOR WITH FLAME MONITOR

BACKGROUND OF INVENTION

This invention relates generally to gas chromatography methods and apparatus, and more specifically relates to the flame ionization detectors which may be utilized with gas chromatography systems.

Among the most common and effective devices currently used with gas chromatography systems for detecting and measuring the separated components in the effluent gas, are the so-called flame ionization detectors (FID). These detectors basically consist of a diffusion-type hydrogen burner, so arranged that the flame is burned between two electrodes, with a typical potential difference of the order of 100–300 volts being maintained between the electrodes. The effluent gas from the chromatography column is mixed with the hydrogen stream to the burner nozzle, and the resultant mixture is burned in air or oxygen. When the column effluent contains organic substances, these will ionize in the hydrogen flame of the detector, changing the conductivity of the flame, and consequently the intensity of the ion current. The ion current between the two electrodes, one of which is usually the burner nozzle itself, can be recorded after appropriate amplification.

A significant problem which in the past has been encountered in use of FID systems is one of assuring that the flame is actually operating. Relatively crude and unacceptable techniques have been utilized for such purposes.

Practitioners in the art, for example, have commonly sought to detect the flame's condition by such cumbersome and time-consuming techniques as inserting small bits of paper into the detector flame zone, removing same and observing the paper for charring. In a similar vein, a mirror has been intermittently positioned over the flame ionization detector for purposes of collecting water vapor — the presence of same being taken as an indication of a burning flame. Where techniques such as these established that the flame was extinquished, re-ignition could be effected via an ignition coil positioned proximate the burner nozzle — i.e. by passing a current through the coil to render same in a hot or glowing condition.

While it has been proposed, e.g. in U.S. Pat. No. 3,340,013, to minimize the flame-out problem by periodically re-igniting the burner, such approach is based upon use of overly complex and costly techniques, i.e. upon a programming system designed to effect heating of the ignition coil at the end of each chromatographic cycle — regardless of the actual condition of the flame. An obvious correlative difficulty with this approach is that re-ignition may not be effected at the time it is actually needed.

In accordance with the foregoing, it may be regarded as an object of the present invention, to provide an improved flame ionization detector for use in gas chromatography systems, which includes simple, dependable, and highly effective means for indicating that the detector flame has become extinguished, to thereby enable manual or automatic re-ignition of such flame.

It is a further object of the invention, to provide an improved flame ionization detector of the aforementioned type, wherein the means for detecting flame extinction is combined with a re-ignition coil, with but a pair of electrical leads being required to enable both functions.

It is a yet further object of the present invention, to provide a flame ionization detector system of the aforementioned type, wherein flame polarization may be effected through the same lead pair utilized for the flame extinction detection function, and the flame re-ignition function.

SUMMARY OF INVENTION

Now in accordance with the present invention, the foregoing objects and others as will become apparent in the course of the ensuing specification, are achieved in a flame ionization detector of the type including an electrode gap, means for applying an electrical potential across the gap, a burner nozzle for providing a flame in the vicinity of the gap, means for introducing the effluent gas into the flame, and means for measuring the ion current through the electrode gap. In accordance with the improvement of the invention, a structure is provided which enables monitoring of the flame condition, so as to enable ignition of an extinguished flame via automatic or manual means.

In particular an igniter coil is mounted proximate the burner nozzle, and thermocouple means are provided including a hot junction in thermal contact with the burner nozzle, and a cold junction spaced from the nozzle. The thermocouple thereby senses the change in temperature at the burner nozzle which occurs upon the flame being extinguished. A signal generating means receives the output from the thermocouple and generates a signal indicative of a flame-out condition. Means are provided for applying an electrical potential to the igniter coil to enable ignition of the flame, upon a flame-out condition being detected. The last-mentioned means may either be actuated manually upon the system operator noting a flame-out condition as measured by the aforementioned signal; or the re-ignition operation may be effected automatically.

In a preferable embodiment of the invention, the ends of the igniter coil are connected to a pair of electrical leads comprising a suitably dissimilar metal from that of the coil. The connection zones may thus define the hot and cold junctions of the thermocouple. This permits the same pair of leads (which pass through the detector casing and are insulated therefrom) to provide both the electrical potential for effecting the igniter function of the coil, and as well the interconnection between the thermocouple and signal generating means.

The burner nozzle is preferably electrically conductive, and thus may comprise one electrode of the pair defining the electrode gap. Thus the means applying the aforementioned electrical potential across the electrode gap, may be connected to the burner nozzle through an electrical path which includes at least one of the electrical leads — whereby said single lead pair serves yet an additional function, i.e. in enabling polarization of the flame.

BRIEF DESCRIPTION OF DRAWINGS

This invention is diagrammatically illustrated, by way of example, in the drawings appended hereto, in which.

DESCRIPTION OF PREFERRED EMBODIMENT

Figure 1:
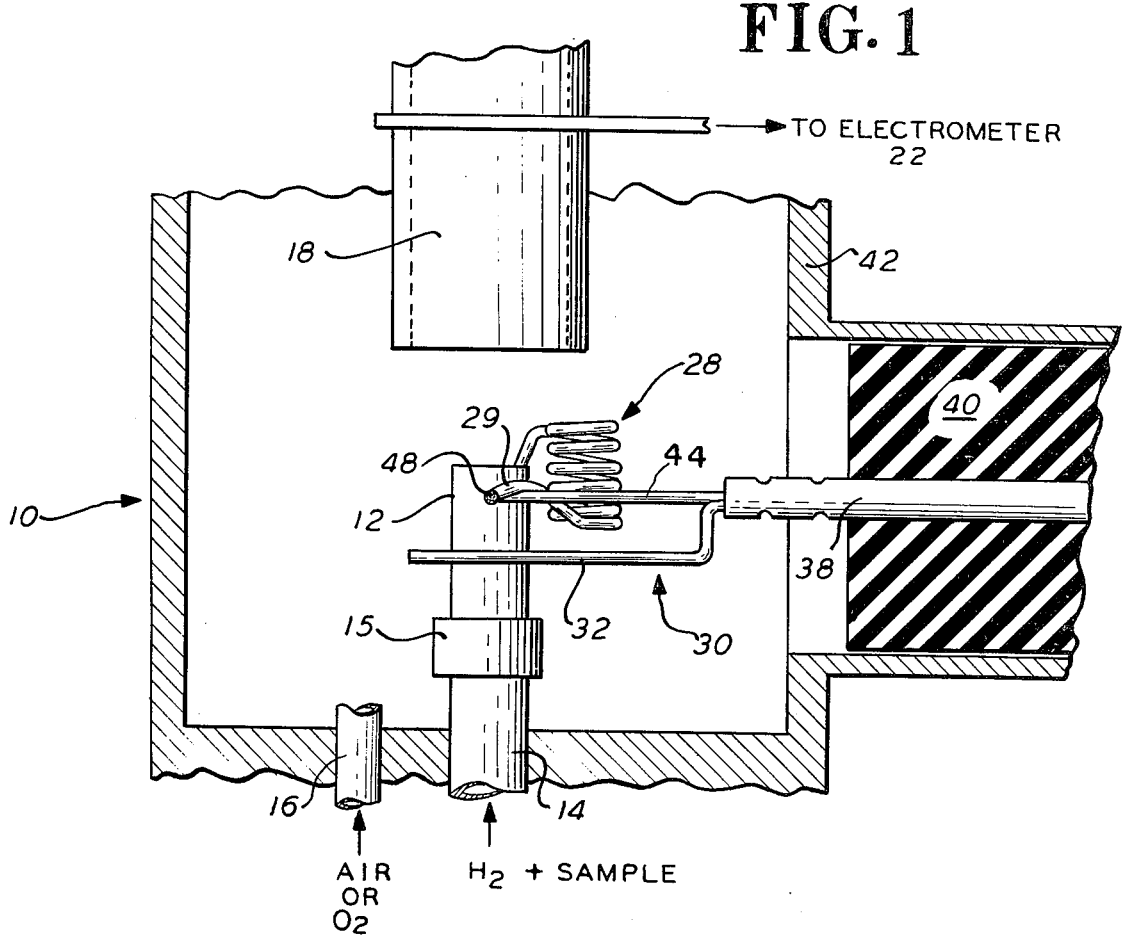
FIG. 1 is a side elevational view, schematic in nature, of those portions of a detector system in accordance with the invention, which serve to provide the flame-out detection, flame igniter and polarization functions.
Figure 2:
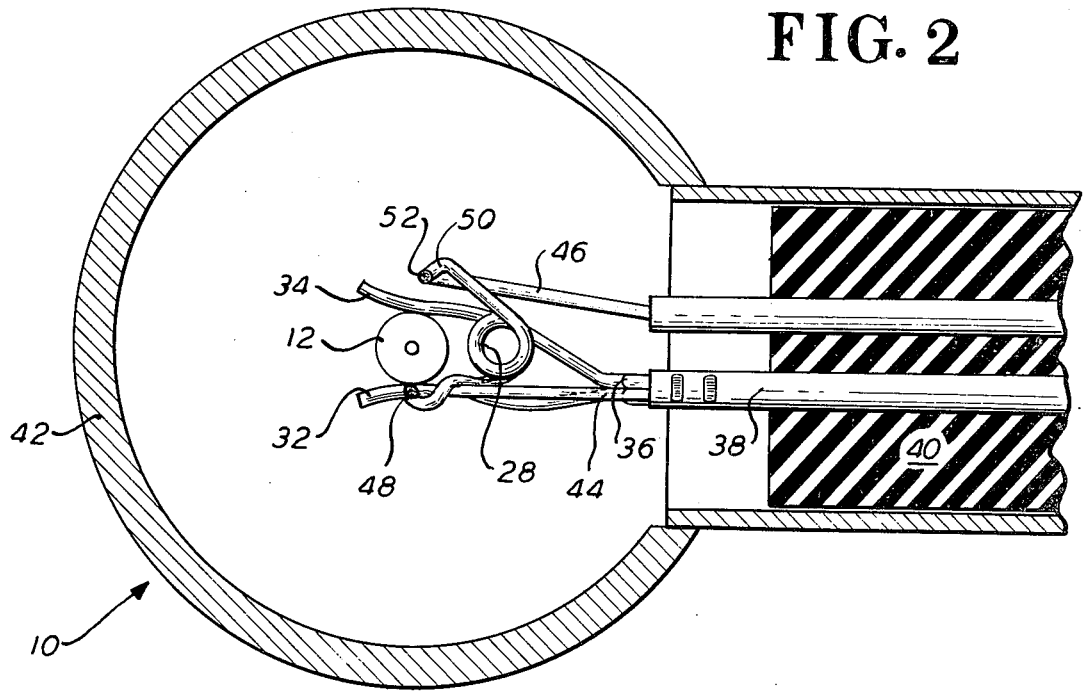
FIG. 2 is a top plan view of the elements depicted in FIG. 1 (with the collector electrode removed for clarity)

In FIGS. 1 and 2 herein, schematic side elevational and plan views appear, which set forth the basic elements of a flame ionization detector 10 in accordance with the invention. The simplified electrical schematic block diagram of FIG. 3 may be considered simultaneously with FIGS. 1 and 2, in order to gain a better understanding of the invention. Corresponding elements in the several Figures are identified by corresponding reference numerals.

The detector 10 of the invention, is in a number of respects of conventional design; and accordingly those elements which are conventional and therefore well understood in the prior art, are not set forth with any great particularity herein. Thus it is seen that detector 10 in accordance with such prior constructions, includes a burner nozzle 12, which is provided with hydrogen from a regulated source (not shown), the gas entering the burner nozzle via a conduit 14. This conduit may also be provided with the effluent gas from the chromatographic column forming part of the chromatographic system with which detector 10 is utilized. Similarly, oxygen and/or air which supports the combustion from the burner nozzle, is provided to the nozzle by a conduit schematically illustrated at 16. The manner of mixing of the said gases in the burner nozzle is well-known in the art, and further details are accordingly not considered necessary herein.

As is again usual in devices of the present type, an electrode gap is provided, with the flame emanating from nozzle 12 being in such a position that the flame products are present in the gap, to thereby enable an ionization current to flow across the gap when a suitable electrical potential is provided thereacross. In the present instance, as is generally common in the art, burner nozzle 12 is electrically conductive and is made to constitute one of the electrodes defining the electrode gap, with an annularly formed collector electrode 18 being positioned somewhat above and spaced from the uppermost portion of nozzle 12, and constituting the other member of the electrode pair. Conduit 14, which joins nozzle 12 via the coupling 15, is preferably electrically non-conductive — as this allows nozzle 12 to be biased independently of the potential of casing 42 through which conduit 14 passes.

Figure 3:
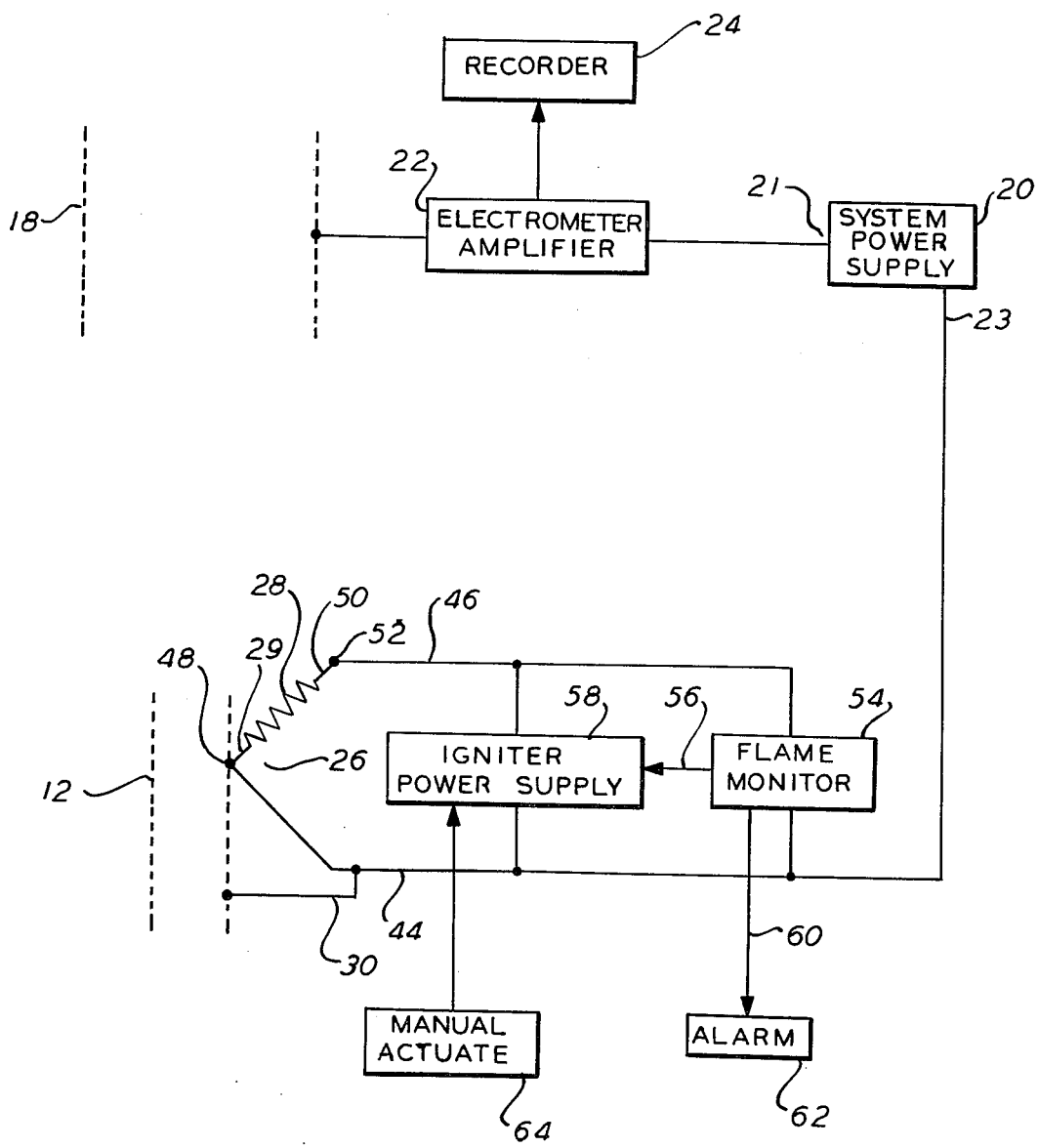
FIG. 3 is a simplified electrical block diagram, schematic in nature, illustrating the principal electrical elements of the detector.

As may be better understood from reference to FIG. 3, a potential difference of the order of 300 volts or so is provided between the aforementioned electrodes, by means of a system power supply 20. The collector electrode 18 is connected to one side 21 of power supply 20 through an electrometer amplifier 22, with nozzle 12 being biased to the opposite polarity from the other side 23 of power supply 20 — by means of connections which will be hereinbelow further discussed. The ionization current that flows through the electrode gap during a chromatographic run is measured by electrometer amplifier 22, the output of which can be provided to a recorder 24, which may be a strip recorder or of other conventional construction.

In accordance with the improvement enabled by the present invention, a thermocouple 26 is provided, which is part of a composite structure serving a plurality of purposes including the detection of a flame-out condition in detector 10. Thermocouple 26 in particular, is associated with an igniter coil 28, which per se is a relatively high resistance element which functions to ignite or re-ignite the flame at nozzle 12 upon a potential being applied across the said coil.

As may be seen from FIGS. 1 and 2, a single pair of leads 44, 46 passes into casing 42 through the insulator 40. The lead 44 is joined to the lower terminal end 29 of coil 28; the lead 46 is joined to the opposite, upper terminal end 50 of coil 28. Coil 28 which may, for example, comprise a nickel-chromium alloy such as Nichrome, is proximate (but slightly spaced) from burner nozzle 12. The joining zone between lead 44 and end 29 of coil 28, is in thermal (and electrical) contact with nozzle 12, and constitutes the hot junction 48 for thermocouple 26. This in view of the fact that lead 44 comprises a suitable dissimilar metal such as constantine, to thereby constitute with the aforementioned Nichrome constituting coil 28, a suitable thermocouple pair.

The joining zone defined between lead 46 and upper terminal end 50 of coil 28 is seen to be spaced from hot junction 48, and thus is spaced from burner nozzle 12. In that lead 46 may again constitute an alloy such as constantine, the zone adjoining thus constitutes the cold junction 52 for thermocouple 26. These relationships may be further understood by cross-reference to the schematic showing of FIG. 3.

In accordance with a principal aspect of the present invention, the single pair of leads 44, 46 serve a variety of functions; i.e. they serve as the lead-outs for the signal from thermocouple 26; they serve to provide a potential across coil 28 enabling the igniter function of same; and finally they will be seen to enable the biasing potential to nozzle 12. The last cited function is facilitated by an electrically conductive spring clip 30, the rearward end 36 of which is crimped into tubing 38 with lead 44 — in consequence of which electrical continuity is present between the said lead and clip. The arms 32 and 34 of clip 30 mechanically and electrically secure the clip to nozzle 12, thus assuring electrical continuity between the nozzle and lead 44. In electrical terms clip 30, as can be seen from the schematic representation of FIG. 3, is thus in parallel with the electrical path including lead 44 and hot junction 48.

In accordance with the foregoing, and referring particularly to FIG. 3, it is seen that the signal developed by thermocouple 26 is provided to a flame monitor 54. In particular the potential developed by the said thermocouple, being a function of the temperature at nozzle 12, will directly indicate to flame monitor 54 the condition of the said flame. An electrical signal may be thus generated from monitor 54 (which may e.g. be a bridge or other measuring circuit), which is indicative of the flame condition. This generated signal can then be utilized in several ways. In an automatic mode of operation the signal may thus be provided via line 56 to actuate and igniter power supply 58 which is connected across the leads 44 and 46, so as to apply a potential across igniter coil 28, which thereupon is heated to a temperature approximate to re-ignite the flame. In the simplest instance the generated signal proceeding through line 56 may e.g. constitute the amplified output from thermocouple 26 — with the igniter power supply 58 being enabled by a mechanical or solid state relay, the actuating current for which is the signal in line 56.

The generated signal from flame monitor 54 may also be provided via parallel output 60, to an alarm 62, which may constitute a visual, audio, or other indicating device for the operator of the chromatographic system. Alarm 62 thus apprises the operator of the flame-out condition of the system. The operator upon being so apprised, may manually actuate the igniter power supply 58, as by means of manual actuator 64 — i.e. a simple switch or so forth. It of course will be evident, that alarm 62 may also function simultaneously with the automatic mode of operation; or the automatic mode of operation may be dispensed with entirely in an alternate embodiment of the present device, with reliance being placed upon manual re-ignition of an extinguished flame.

As has previously been indicated, the arrangement of the present invention enables yet a further function to be performed by the single pair of connecting leads 44 and 46. In particular, and as may be seen by reference to FIG. 3, biasing of burner nozzle 12 can in the present arrangement, be enabled through the same connector 44, 46. Thus the side 23 of system power supply 20 may be connected to nozzle 12 via the lead 44. The electrical biasing connection can thus be regarded as proceeding through the hot junction 48 and/or through the parallel connection enabled by spring clip 30. Alternatively it is possible to connect and bias nozzle 12 through the alternate lead 46, and effect an equivalent function. As is also known in the present art, the relative polarity between electrodes may be in either direction, provided that the various elements in the circuit are appropriately connected to measure the ionization current, and to assure proper grounding of elements that might be operator contacted.

While the present invention has been particularly set forth in terms of specific embodiments thereof, it will be understood in view of the present disclosure, that numerous variations upon the invention are now enabled to those skilled in the art, which variations yet reside within the scope of the present teaching. Accordingly the invention is to be broadly construed, and limited only by the scope and spirit of the claims now appended hereto.

We claim:

1. In a flame ionization detector for use in detecting separated components in the effluent from a gas chromatography column, said detector being of the type including an electrode gap, means for applying an electrical potential across said gap, a burner nozzle for providing a flame in the vicinity of said gap, means for introducing said effluent gas into said flame, and means for measuring the ion current through said electrode gap; the improvement enabling monitoring of said flame condition and ignition of an extinguished flame, comprising:

an igniter coil mounted proximate to said burner nozzle for igniting an extinguished flame;

thermocouple means including a hot junction in thermal contact with said burner nozzle, and a cold junction spaced from said nozzle, for sensing the temperature at said nozzle;

signal generating means for receiving the output from said thermocouple and generating a signal indicative of a flame-out condition;

means for applying an electrical potential to said igniter coil to heat said coil and thereby enable ignition of said flame upon said flame-out condition being indicated; and a pair of electrical leads connected to provide both said electrical potential for heating said coil, and the interconnection between said thermocouple and said signal generating means.

2. Apparatus in accordance with claim 1, wherein the ends of said coil are connected to said leads to define said hot and cold junctions.

3. Apparatus in accordance with claim 2, wherein said signal indicative of said flame-out condition controls said means applying said electrical potential across said igniter coil, whereby said igniter coil is actuated automatically upon detection of said flame-out condition.

4. Apparatus in accordance with claim 2, wherein said burner nozzle is electrically conductive and comprises one electrode of the pair defining said electrode gap; and wherein said means applying said electrical potential across said gap is connected to said burner nozzle through an electrical path including at least one of said leads.

5. Apparatus in accordance with claim 4, further including a spring clip engaging said burner nozzle and in electrical continuity with said one lead, for assuring electrical continuity of said electrical path biasing said nozzle.

6. Apparatus in accordance with claim 2, including alarm means responsive to said generated signal, whereby to apprise an operator of a flame-out condition.

7. Apparatus in accordance with claim 6, further including manually actuated means for enabling said means for applying said potential to said ingiter coil, whereby said operator may effect re-ignition manually upon said alarm means establishing said flame-out condition.

8. In a gas chromatography apparatus of the type including a flame ionization detector for detecting separated components in the effluent from the chromatography column, said detector including a burner nozzle for a flame source, said nozzle being electrically conductive and constituting a first electrode, a second electrode being spaced from said first electrode, means for applying an electrical potential between said electrodes, means for introducing said effluent gas into said flame, and means for measuring and evaluating the ionization current between said electrodes; the improvement enabling monitoring of said flame, and ignition of an extinguished flame, comprising:

an igniter coil mounted proximate said burner nozzle, one end of said coil being in thermal contact with said burner nozzle, and the opposite end of said coil being spaced from said nozzle;

a pair of electrical leads connected to the said ends of said coil, said leads comprising a dissimilar metal from that of said coil and the connections between said coil and leads defining the hot and cold junctions of a thermocouple for sensing changes in temperature at said nozzle;

igniter power supply means for passing a relatively high current through said igniter coil to enable heating of same to ignite said flame; and means connected by said leads to said thermocouple and responsive to said thermocouple output by enabling said igniter power supply means upon the occurrence of said flame-out condition.

9. Apparatus in accordance with claim 8, wherein said means applying said potential between said electrodes is connected to said burner nozzle through an electrical path including at least one of said leads.

10. Apparatus in accordance with claim 9, further including spring clip means mechanically and electrically engaging said burner nozzle and in parallel with said one lead, for assuring electrical continuity in the said electrical path biasing said nozzle.

11. In a gas chromatography apparatus of the type including a flame ionization detector for detecting separated components of the effluent gas from the chromatography column; said detector including a burner nozzle for a flame source, said nozzle being electrically conductive and constituting a first electrode, a second electrode spaced from said first electrode, means for applying an electrical potential between said electrodes, means for introducing effluent gas into the said flame, and means for measuring and evaluating the ionization current between said electrodes; the improvement enabling detection of a flame-out condition, and ignition of an extinguished flame, comprising:

thermocouple means including a hot junction in thermal contact with said burner nozzle, and a cold junction spaced from said nozzle, for enabling sensing of changes in temperature at said nozzle; the conductive path between said thermocouple junctions being defined by an igniter coil mounted adjacent said burner nozzle;

thermocouple output signal receiving means connected to receive the output from said thermocouple to thereby indicate a flame-out condition;

means for passing a relatively high current through said igniter coil to enable igniting of said flame; and a pair of electrical leads being connected to provide both the electrical potential for heating said coil, and transmission of the thermocouple signal to said thermocouple output signal receiving means.

12. Apparatus in accordance with claim 11, wherein said hot junction is in electrical continuity with said nozzle, and said means for applying said electrical potential between said electrodes is connected to bias said nozzle electrode through said hot junction.

13. Apparatus in accordance with claim 11, including spring clip means electrically and mechanically engaging said burner nozzle; and wherein said means for applying said electrical potential between said electrodes is connected to bias said nozzle electrode through an electrical path including said spring clip means.

14. Apparatus in accordance with claim 13, wherein said spring clip means is electrically continuous with the said lead connected to the hot junction side of said coil.

* * * * *

UNITED STATES PATENT AND TRADEMARK OFFICE
CERTIFICATE OF CORRECTION

PATENT NO. : 3,985,509
DATED : October 12, 1976
INVENTOR(S) : Elmer Trone and Robert Leslie Howe It is certified that error appears in the above-identified patent and that said Letters Patent are hereby corrected as shown below:

Column 6, line 34: Change "ingiter" to --igniter--.

Signed and Sealed this

Eighth Day of November 1977

[SEAL]

Attest:

RUTH C. MASON
Attesting Officer

LUTRELLE F. PARKER
Acting Commissioner of Patents and Trademarks